United States Patent [19]

Gaffar et al.

[11] Patent Number: 5,288,480
[45] Date of Patent: * Feb. 22, 1994

[54] ANTIPLAQUE ANTIBACTERIAL ORAL COMPOSITION

[75] Inventors: Abdul Gaffar, Princeton; Nuran Nabi, Brunswick; John Afflitto, Brookside, all of N.J.; Orum Stringer, Yardley, Pa.

[73] Assignee: Colgate-Palmolive Co., New York, N.Y.

[*] Notice: The portion of the term of this patent subsequent to Jul. 16, 2008 has been disclaimed.

[21] Appl. No.: 964,247

[22] Filed: Oct. 21, 1992

Related U.S. Application Data

[60] Division of Ser. No. 655,571, Feb. 19, 1991, Pat. No. 5,178,851, which is a continuation of Ser. No. 398,566, Aug. 25, 1989, Pat. No. 5,032,386, which is a continuation-in-part of Ser. No. 291,712, Dec. 29, 1988, Pat. No. 4,894,220, and a continuation-in-part of Ser. No. 346,258, May 1, 1989, Pat. No. 5,043,154, which is a continuation of Ser. No. 8,901, Jan. 30, 1987, abandoned.

[51] Int. Cl.$^5$ .......................... A61K 7/16; A61K 7/18
[52] U.S. Cl. .......................................... 424/52; 424/49
[58] Field of Search ...................................... 424/49–58

[56] References Cited

U.S. PATENT DOCUMENTS

| | | | |
|---|---|---|---|
| 3,629,477 | 12/1971 | Model et al. | 424/340 |
| 4,022,880 | 5/1977 | Vinson et al. | 424/49 |
| 5,032,386 | 7/1991 | Gaffar et al. | 424/49 |
| 5,096,699 | 3/1992 | Gaffar et al. | 424/49 |
| 5,178,851 | 1/1993 | Gaffar et al. | 424/52 |
| 5,180,578 | 1/1993 | Gaffar et al. | 424/52 |
| 5,188,821 | 2/1993 | Gaffar et al. | 424/52 |
| 5,192,530 | 3/1993 | Gaffar et al. | 424/52 |
| 5,192,531 | 3/1993 | Gaffar et al. | 424/52 |
| 5,208,009 | 5/1993 | Gaffar et al. | 424/19 |

*Primary Examiner*—Shep K. Rose
*Attorney, Agent, or Firm*—Robert L. Stone; Murray M. Grill

[57] ABSTRACT

An oral composition dentifrice comprising an orally acceptable vehicle, about 5–30% by weight of a siliceous polishing agent, about 0.25–0.35% by weight of a substantially water-insoluble noncationic antibacterial antiplaque agent, such as 2,4,4'-trichloro-2'-hydroxydiphenyl ether (triclosan) and an antibacterial-enhancing agent which enhances the delivery of said antibacterial agent to, and retention thereof on, oral surfaces.

15 Claims, No Drawings

ANTIPLAQUE ANTIBACTERIAL ORAL COMPOSITION

This is a division of Application Ser. No. 07/655,571, filed Feb. 19, 1991, now U.S. Pat. No. 5,178,851, issued Jan. 12, 1993, which is a continuation of Application Ser. No. 07/398,566, filed Aug. 25, 1989, now U.S. Pat. No. 5,032,386, granted Jul. 16, 1991, which is a continuation-in-part of Application Ser. No. 07/291,712, filed Dec. 29, 1988, now U.S. Pat. No. 4,894,220, granted Jan. 16, 1990, and of Application Ser. No. 07/346,258, filed May 1, 1989, now U.S. Pat. No. 5,043,154, granted Aug. 27, 1991, which are respectively a continuation-in-part and a continuation of application Ser. No. 07/008,901, filed Jan. 30, 1987, now abandoned.

This invention relates to an antibacterial antiplaque oral composition dentifrice. More particularly, it relates to an oral composition dentifrice containing a substantially water-insoluble noncationic antibacterial agent effective to inhibit plaque.

Dental plaque is a soft deposit which forms on teeth as opposed to calculus which is a hard calcified deposit on teeth. Unlike calculus, plaque may form on any part of the tooth surface, particularly including at the gingival margin. Hence, besides being unsightly, it is implicated in the occurrence of gingivitis.

Accordingly, it is highly desirable to include antimicrobial agents which have been know to reduce plaque in oral compositions. Frequently, cationic antibacterial agents have been suggested. Moreover, in U.S. Pat. No. 4,022,880 to Vinson et al, a compound providing zinc ions as an anticalculus agent is admixed with an antibacterial agent effective to retard the growth of plaque bacteria. A wide variety of antibacterial agents are described with the zinc compounds including cationic materials such as guanides and quaternary ammonium compounds as well as non-cationic compounds such as halogenated salicylanilides and halogenated hydroxydiphenyl ethers. The noncationic antibacterial antiplaque halogenated hydroxydiphenyl ether, triclosan, has also been described in combination with zinc citrate trihydrate in European Patent Publication 0161,899 to Saxton et al. Triclosan is also disclosed in European Patent Publication 0271,332 to Davis as a toothpaste component, containing a solubilizing agent such as propylene glycol.

The cationic antibacterial materials such as chlorhexidine, benzthonium chloride and cetyl pyridinium chloride have been the subject of greatest investigation as antibacterial antiplaque agents. However, they are generally not effective when used with anionic materials. Noncationic antibacterial materials, on the other hand, can be compatible with anionic components in an oral composition.

However, oral compositions typically are mixtures of numerous components and even such typically neutral materials as humectants can affect performance of such compositions.

Moreover, even noncationic antibacterial agents may have limited antiplaque effectiveness with commonly used materials such as polyphosphate anticalculus agents which are disclosed together in British Patent Publication 22 00551 of Gaffar et al and in EP 0251591 of Jackson et al. In commonly assigned Ser. No. 07/398,605 filed on Aug. 25, 1989, titled "Antibacterial, Antiplaque Anticalculus Oral Composition", it is shown the antiplaque effectiveness is greatly enhanced by including an antibacterial-enhancing agent (AEA) which enhances the delivery of said antibacterial agent to, and retention thereof on, oral surfaces and providing optimized amounts and ratio of polyphosphate and AEA.

Further, even when polyphosphate anticalculus agent is not present as in commonly assigned Ser. No. 07/398,606 filed on Aug. 25, 1989, titled "Antibacterial Antiplaque Oral Composition", antiplaque effectiveness on soft oral tissue is optimized by including with the AEA a solubilizing material which dissolves the noncationic antibacterial agent in saliva when the polishing agent is a siliceous polishing agent present in amount of about 5–30%. When the amount of polishing material is about 30–75% by weight, the special solubilizing material is not required, as in commonly assigned Ser. No. 07/399,669, filed on Aug. 25, 1989, titled "Antibacterial Antiplaque Oral Composition".

It is an advantage of this invention that an oral composition dentifrice containing a siliceous polishing agent, a small but effective antiplaque amount of a substantially water-insoluble noncationic antibacterial agent and an AEA is provided to inhibit plaque formation, even without requiring the presence of special solubilizing agent.

It is an advantage of this invention that the AEA enhances the delivery and retention of small but effective antiplaque amount of the antibacterial agent on teeth and on soft oral tissues.

It is a further advantage of this invention that an antiplaque oral composition is provided which is effective to reduce the occurrence of gingivitis.

Additional advantages of this invention will be apparent from consideration of the following specification.

In accordance with certain of its aspects, this invention relates to an oral composition dentifrice comprising in an orally acceptable vehicle, about 5–30% by weight of a siliceous polishing agent, about 0.25–0.35% by weight of a substantially water insoluble noncationic antibacterial agent, said oral composition dentifrice comprising at least one of a surface active-agent and a flavoring oil, and about 0.05–4% by weight of said AEA, said oral composition dentifrice being substantially free of polyphosphate anticalculus agent.

Typical examples of water insoluble noncationic antibacterial agents which are particularly desirable from considerations of antiplaque effectiveness, safety and formulation are:

HALOGENATED DIPHENYL ETHERS

2',4,4'-trichloro-2-hydroxy-diphenyl ether (Triclosan)
2,2'-dihydroxy-5,5'-dibromo-diphenyl ether.

HALOGENATED SALICYLANILIDES

4'5-dibromosalicylanilide
3,4',5-trichlorosalcylanilide
3,4',5-tribromosalicylanilide
2,3,3',5-tetrachlorosalicylanilide
3,3',5-tetrachlorosalicylanilide
3,5-dibromo-3'-trifluoromethyl salicylanilide
5-n-octanoyl-3'-trifluoromethyl salicylanilide
3,5-dibromo-4'-trifluoromethyl salicylanilide
3,5-dibromo-3'-trifluoro methyl salicylanilide (Flurophene).

BENZOIC ESTERS

Methyl—p-Hydroxybenzoic Ester
Ethyl—p-Hydroxybenzoic Ester

Propyl—p-Hydroxybenzoic Ester
Butyl—p-Hydroxybenzoic Ester.

HALOGENATED CARBANILIDES 3,4,4'-trichlorocarbanilide
3-trifluoromethyl-4,4'-dichlorocarbanilide
3,3',4-trichlorocarbanilide.

Phenolic Compounds (including phenol and its homologs, mono-and poly-alkyl and aromatic halo (e.g. F,Cl,Br,I)-phenols, resorcinol and catechol and their derivatives and bisphenolic compounds). Such phenolic compounds includes inter alia:

PHENOL AND ITS HOMOLOGS

Phenol
2 Methyl—Phenol
3 Methyl—Phenol
4 Methyl—Phenol
4 Ethyl—Phenol
2,4-Dimethyl—Phenol
2,5-Dimethyl—Phenol
3,4-Dimethyl—Phenol
2,6-Dimethyl—Phenol
4-n-Propyl—Phenol
4-n-Butyl—Phenol
4-n-Amyl—Phenol
4-tert-Amyl—Phenol
4-n-Hexyl—Phenol
4-n-Heptyl—Phenol
2-Methoxy-4-(2-Propenyl)-Phenol (Eugenol)
2-Isopropyl-5-Methyl-Phenol (Thymol).

MONO- AND POLY-ALKYL AND ARALKYL HALOPHENOLS

Methyl—p-Chlorophenol
Ethyl—p-Chlorophenol
n-Propyl—p-Chlorophenol
n-Butyl—p-Chlorophenol
n-Amyl—p-Chlorophenol
sec-Amyl—p-Chlorophenol
n-Hexyl—p-Chlorophenol
Cyclohexyl—p-Chlorophenol
n-Heptyl—p-Chlorophenol
n-Octyl—p-Chlorophenol
O-Chlorophenol
Methyl—o-Chlorophenol
Ethyl—o-Chlorophenol
n-Propyl—o-Chlorophenol
n-Butyl—o-Chlorophenol
n-Amyl—o-Chlorophenol
tert-Amyl—o-Chlorophenol
n-Hexyl—o-Chlorophenol
n-Heptyl—o-Chlorophenol
p-Chlorophenol
o-Benzyl—p-Chlorophenol
o-Benzyl-m-methyl—p-Chlorophenol
o-Benzyl-m, m-dimethyl—p-Chlorophenol
o-Phenylethyl—p-Chlorophenol
o-Phenylethyl-m-methyl—p-Chlorophenol
3-Methyl—p-Chlorophenol
3,5-Dimethyl—p-Chlorophenol
6-Ethyl-3-methyl—p-Chlorophenol
6-n-Propyl-3-methyl—p-Chlorophenol
6-iso-Propyl-3-methyl—p-Chlorophenol
2-Ethyl-3,5-dimethyl—p-Chlorophenol
6-sec Butyl-3-methyl—p-Chlorophenol
2-iso-Propyl-3,5-dimethyl—p-Chlorophenol
6-Diethylmethyl-3-methyl—p-Chlorophenol
6-iso-Propyl-2-ethyl-3-methyl—p-Chlorophenol
2-sec Amyl-3,5-dimethyl—p-Chlorophenol
2-Diethylmethyl-3,5-dimethyl—p-Chlorophenol
6-sec Octyl-3-methyl—p-Chlorophenol
p-Bromophenol
Methyl—p-Bromophenol
Ethyl—p-Bromophenol
n-Propyl—p-Bromophenol
n-Butyl—p-Bromophenol
n-Amyl—p-Bromophenol
sec-Amyl—p-Bromophenol
n-Hexyl—p-Bromophenol
cyclohexyl—p-Bromophenol
o-Bromophenol
tert-Amyl—o-Bromophenol
n-Hexyl—o-Bromophenol
n-Propyl-m,m-Dimethyl—o-Bromophenol
2-Phenyl Phenol
4-chloro-2-methyl phenol
4-chloro-3-methyl phenol
4-chloro-3,5-dimethyl phenol
2,4-dichloro-3,5-dimethylphenol
3,4,5,6-terabromo-2-methylphenol
5-methyl-2-pentylphenol
4-isopropyl-3-methylphenol
5-chloro-2-hydroxydiphenylemthane.

RESORCINOL AND ITS DERIVATIVES

Resorcinol
Methyl—Resorcinol
Ethyl—Resorcinol
n-Propyl—Resorcinol
n-Butyl—Resorcinol
n-Amyl—Resorcinol
n-Hexyl—Resorcinol
n-Heptyl—Resorcinol
n-Octyl—Resorcinol
n-Nonyl—Resorcinol
Phenyl—Resorcinol
Benzyl—Resorcinol
Phenylethyl—Resorcinol
Phenylpropyl—Resorcinol
p-Chlorobenzyl—Resorcinol
5-Chloro—2,4-Dihydroxydiphenyl Methane
4'-Chloro—2,4-Dihydroxydiphenyl Methane
5-Bromo—2,4-Dihydroxydiphenyl Methane
4'-Bromo—2,4-Dihydroxydiphenyl Methane.

BISPHENOLIC COMPOUNDS

Bisphenol A
2,2'-methylene bis (4-chlorophenol)
2,2'-methylene bis (3,4,6-trichlorophenol) (hexachlorophene)
2,2'-methylene bis (4-chloro-6-bromophenol)
bis (2-hydroxy-3,5-dichlorophenyl) sulfide
bis (2-hydroxy-5-chlorobenzyl) sulfide.

The noncationic antibacterial agent is present in the oral composition in an effective antiplaque amount of about 0.25–0.35% by weight, preferably about 0.3%.

The antibacterial agent is substantially water-insoluble, meaning that its solubility is less than about 1% by weight in water at 25° C. and may be even less than about 0.1%.

The preferred halogenated diphenyl ether is triclosan. The preferred phenolic compounds are phenol, thymol, eugenol, hexyl resorcinol and 2,2'-methylene bis(4-chloro-6-bromophenol). The most preferred antibacterial antiplaque compound is triclosan. Triclosan is disclosed in aforementioned U.S. Pat. No. 4,022,880 as an antibacterial agent in combination with an anticalculus agent which provides zinc ions, and in German Patent Disclosure 3532860 in combination with a copper compound. In European Patent Disclosure 0278744 it is disclosed in combination with a tooth densitizing agent containing a source of potassium ions. It is also disclosed as an antiplaque agent in a dentifrice formulated to contain a lamellar liquid crystal surfactant phase having a lamellar spacing of less than 6.0 nm and which may optionally contain a zinc salt in published European Patent Application 0161898 of Lane et al and in a dentifrice containing zinc citrate trihydrate in published European Patent Application 0161899 to Saxton et al.

The antibacterial-enhancing agent (AEA) which enhances delivery of said antibacterial agent to, and retention thereof on, oral surfaces, is employed in amounts effective to achieve such enhancement within the range in the oral composition of about 0.05% to about 4%, preferably about 0.1% to about 3%, more preferably about 0.5% to about 2.5% by weight.

AEA polymeric materials of the present invention include those which can be characterized as having utility as dentifrice adhesives or fixatives or dental cements. For example, U.S. Pat. Nos. 4,521,551 and 4,375,036, each to Chang et al, describe commercially available copolymer of methylvinyl ether-maleic anhydride (Gantrez) as a denture fixative. However, there has not been recognition in the prior art that adhesives, fixatives or cements when applied in water-soluble or water-swellable form together with substantially water-insoluble non-cationic antibacterial antiplaque agents could enhance the antibacterial activity of such agents. Further, in U.S. Pat. No. 4,485,090 to Chang, Gantrez AN copolymer is mentioned among polymeric anionic membrane-forming materials which attach to a tooth surface to form a hydrophobic barrier which reduces elution of a previously applied therapeutic caries prophylactic fluoride compound. Again, there is no recognition that such polymeric material could enhance the antibacterial activity of substantially water-insoluble non-cationic antibacterial antiplaque agents.

This AEA may be a simple compound, preferably a polymerizable monomer, more preferably a polymer, which latter term is entirely generic, including for example oligomers, homopolymers, copolymers of two or more monomers, ionomers, block copolymers, graft copolymers, cross-linked polymers and copolymers, and the like. The AEA may be natural or synthetic, and water insoluble or preferably water (saliva) soluble or swellable (hydratable, hydrogel forming). It has an (weight) average molecular weight of about 100 to about 1,000,000, preferably about 1,000 to about 1,000,000, more preferably about 2,000 or 2,500 to about 250,000 or 500,000.

The AEA ordinarily contains at least one delivery-enhancing group, which is preferably acidic such as sulfonic, phosphinic, or more preferably phosphonic or carboxylic, or salt thereof, e.g. alkali metal or ammonium, and at least one organic retention-enhancing group, preferably a plurality of both the delivery-enhancing and retention-enhancing groups, which latter groups preferably have the formula $—(X)_n—R$ wherein X is O, N, S, SO, $SO_2$, P, PO or Si or the like, R is hydrophobic alkyl, alkenyl, acyl, aryl, alkaryl, aralkyl, heterocyclic or their inert-substituted derivatives, and n is zero or 1 or more. The aforesaid "inert-substituted derivatives", are intended to include substituents on R which are generally non-hydrophilic and do not significantly interfere with the desired functions of the AEA as enhancing the delivery of the antibacterial agent to, and retention thereof on, oral surfaces such as halo, e.g. Cl, Br, I, and carbo and the like. Illustrations of such retention-enhancing groups are tabulated below.

| n | X | $—(X)_nR$ |
|---|---|---|
| 0 | — | methyl, ethyl, propyl, butyl, isobutyl, t-butyl, cyclohexyl, allyl, benzyl, phenyl, chlorophenyl, xylyl, pyridyl, furanyl, acetyl, benzoyl, butyryl, terephthaloyl, etc. |
| 1 | O | ethoxy, benzyloxy, thioacetoxy, phenoxy, carboethoxy, carbobenzyloxy, etc. |
|   | N | ethylamino, diethylamino, propylamido, benzoylamido, benzoylaido, phenylacetamido, etc. |
|   | S | thiobutyl, thioisobutyl, thioallyl, thiobenzyl, thiophenyl, thiopropionyl, phenylthioacetyl, thiobenzoyl, etc. |
|   | SO | butylsulfoxy, allylsulfoxy, benzylsulfoxy, phenylsulfoxy, etc. |
|   | $SO_2$ | butylsulfonyl, allysulfonyl, benzylsulfonyl, phenylsulfonyl, etc. |
|   | P | diethyphosphinyl, ethylvinylphosphinyl, ethylallylphosphinyl, ethylbenzylphosphinyl, ethylphenylphosphinyl, etc. |
|   | PO | diethylphosphinoxy, ethylvinylphosphinoxy, methylallylphosphinoxy, methylbenzyphosphinoxy, methylphenylphosphinoxy, etc. |
|   | Si | trimethysilyl, dimethylbutylsilyl, dimethylbenzylsilyl, dimethylvinylsilyl, dimethylallylsilyl, etc. |

As employed herein, the delivery-enhancing group refers to one which attaches or substantively, adhesively, cohesively or otherwise bonds the AEA (carrying the antibacterial agent) to oral (e.g. tooth and gum) surfaces, thereby "delivering" the antibacterial agent to such surfaces. The organic retention-enhancing group, generally hydrophobic, attaches or otherwise bonds the antibacterial agent to the AEA, thereby promoting retention of the antibacterial agent to the AEA and indirectly on the oral surfaces. In some instances, attachment of the antibacterial agent occurs through physical entrapment thereof by the AEA, especially when the AEA is a cross-linked polymer, the structure of which inherently provides increased sites for such entrapment. The presence of a higher molecular weight, more hydrophobic cross-linking moiety in the cross-linked polymer still further promotes the physical entrapment of the antibacterial agent to or by the cross-linked AEA polymer.

Preferably, the AEA is an anionic polymer comprising a chain or backbone containing repeating units each preferably containing at least one carbon atom and preferably at least one directly or indirectly pendant, monovalent delivery-enhancing group and at least one directly or indirectly pendant monovalent retention-enhancing group geminally, vicinally or less preferably otherwise bonded to atoms, preferably carbon, in the chain. Less preferably, the polymer may contain delivery-enhancing groups and/or retention-enhancing groups and/or other divalent atoms or groups as links in the polymer chain instead of or in addition to carbon atoms, or as cross-linking moieties.

It will be understood that any examples or illustrations of AEA's disclosed herein which do not contain both delivery-enhancing groups and retention enhancing groups may and preferably should be chemically modified in known manner to obtain the preferred AEA's containing both such groups and preferably a plurality of each such groups. In the case of the preferred polymeric AEA's, it is desirable, for maximizing substantivity and delivery of the antibacterial agent to oral surfaces, that the repeating units in the polymer chain or backbone containing the acidic delivery enhancing groups constitute at least about 10%, preferably at least about 50%, more preferably at least about 80% up to 95% or 100% by weight of the polymer.

According to a preferred embodiment of this invention, the AEA comprises a polymer containing repeating units in which one or more phosphonic acid delivery-enhancing groups are bonded to one or more carbon atoms in the polymer chain. An example of such an AEA is poly (vinyl phosphonic acid) containing units of the formula:

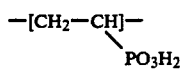   I which however does not contain a retention-enhancing group. A group of the latter type would however be present in poly (1-phosphonopropene) with units of the formula:

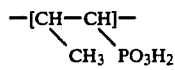   II

A preferred phosphonic acid-containing AEA for use herein is poly (beta styrene phosphonic acid) containing units of the formula:

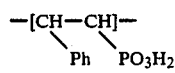   III wherein Ph is phenyl, the phosphonic delivery-enhancing group and the phenyl retention-enhancing group being bonded on vicinal carbon atoms in the chain, or a copolymer of beta styrene phosphonic acid with vinyl phosphonyl chloride having the units of the foregoing formula III alternating or in random association with units of formula I above, or poly (alpha styrene phosphonic acid) containing units of the formula:

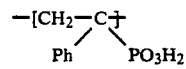   IV in which the delivery—and retention—enhancing groups are geminally bonded to the chain.

These styrene phosphonic acid polymers and their copolymers with other inert ethylenically unsaturated monomers generally have molecular weights in the range of about 2,000 to about 30,000, preferably about 2,500 to about 10,000, and are, with their methods of preparation disclosed and claimed in concurrently filed application Ser. No. 07/398,606 filed Aug. 25, 1989, which disclosure is incorporated here. Such "inert" monomers do not significantly interfere with the intended function of any copolymer employed as an AEA herein.

Other phosphonic-containing polymers include, for example, phosphonated ethylene having units of the formula.

   V where n may for example be an integer or have a value giving the polymer a molecular weight of about 3,000; and sodium poly (butene-4,4-diphosphonate) having units of the formula:

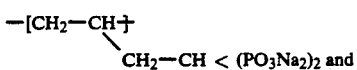   VI poly (allyl bis (phosphonoethyl) amine) having units of the formula:

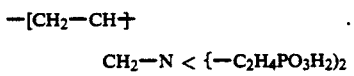   VII

Other phosphonated polymers, for example poly (allyl phosphono acetate), phosphonated polymethacrylate, etc. and the geminal diphosphonate polymers disclosed in EP Publication 0321233 may be employed herein as AEA's, provided of course that they contain or are modified to contain the above-defined organic retention-enhancing groups.

According to another preferred embodiment, the AEA may comprise a synthetic anionic polymeric polycarboxylate. Although not used in the present invention to coact with polyphosphate anticalculus agent, synthetic anionic polymeric polycarboxylate having a molecular weight of about 1,000 to about 1,000,000, preferably about 30,000 to about 500,000, has been used as an inhibitor of alkaline phosphatase enzyme in optimizing the anticalculus effectiveness of linear molecularly dehydrated polyphosphate salts, as disclosed in U.S. Pat. No. 4,627,977 to Gaffar et al. Indeed, in published British Patent Publication 22 00551, the polymeric polycarboxylate is disclosed as an optional ingredient in oral compositions containing linear molecularly dehydrated polyphosphate salts and substantially water-insoluble noncationic antibacterial agent. It is further observed, in the context of the present invention that such polycarboxylate when containing or modified to contain retention-enhancing groups is markedly effective to enhance delivery and retention of the noncationic antibacterial, antiplaque agent to dental surfaces when another ingredient with which the polymeric polycarboxylate would coact (that is, molecularly dehydrated polyphosphate) is absent; for instance, when the ingredient with which the polymeric polycarboxylate coacts is especially the noncationic antibacterial agent.

Synthetic anionic polymeric polycarboxylates and their complexes with various cationic germicides, zinc and magnesium have been previously disclosed as anticalculus agents per se in, for example U.S. Pat. No. 3,429,963 to Shedlovsky; U.S. Pat. No. 4,152,420 to Gaffar; U.S. Pat. No. 3,956,480 to Dichter et al; U.S. Pat. No. 4,138,477 to Gaffar; and U.S. Pat. No. 4,183,914 to Gaffar et al. It is to be understood that the synthetic anionic polymeric polycarboxylates so disclosed in these several patents when containing or modified to contain retention-enhancing groups are operative in the compositions and methods of this invention and such disclosures are to that extent incorporated herein by reference thereto.

The synthetic anionic polymeric polycarboxylates employed herein are well known, being often employed in the form of their free acids or preferably partially or more preferably fully neutralized water soluble or water swellable (hydratable, gel forming) alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 500,000. These copolymers are available for example as Gantrez, e.g. AN 139 (M.W. 500,000), A.N. 119 (M.W. 250,000); and preferably S-97 Pharmaceutical Grade (M.W. 70,000), of GAF Corporation.

Other AEA operative polymeric polycarboxylates containing or modified to contain retention-enhancing groups include those disclosed in U.S. Pat. No. 3,956,480 referred to above, such as the 1:1 copolymers of maleic anhydride with ethyl acrylate, hydroxyethyl methacrylate, N-vinyl-2-pyrollidone, or ethylene, the latter made available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred to U.S. Pat. No. 4,138,477 and 4,183,914, containing or modified to contain retention-enhancing groups include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are retention-enhancing group-containing polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers ordinarily contain sufficient carboxylic salt groups for water-solubility.

Also useful herein are so-called carboxyvinyl polymers disclosed as toothpaste components in U.S. Pat. No. 3,980,767 to Chown et al; U.S. Pat. No. 3,935,306 to Roberts et al; U.S. Pat. No. 3,919,409 to Perla et al; U.S. Pat. No. 3,911,904 to Harrison, and U.S. Pat. No. 3,711,604 to Colodney et al. They are commercially available for example under the trademarks Carbopol 934, 940 and 941 of B. F. Goodrich, these products consisting essentially of a colloidally water-soluble polymer of polyacrylic acid crosslinked with from about 0.75% to about 2.0% of polyallyl sucrose or polyallyl pentaerythritol as cross linking agent, the cross-linked structure and cross-linkages providing the desired retention enhancement by hydrophobicity and/or physical entrapment of the antibacterial agent or the like. Polycarbophil is somewhat similar, being poly acrylic acid cross-linked with less than 0.2% of divinyl glycol, the lower proportion, molecular weight and/or hydrophobicity of this cross-linking agent tending to provide little or no retention enhancement. 2,5-dimethyl-1,5-hexadiene exemplifies a more effective retention-enhancing cross-linking agent.

The synthetic anionic polymeric polycarboxylate component is mainly a hydrocarbon with optional halogen and O-containing substituents and linkages as present in for example ester, ether and OH groups, and is employed in the instant compositions in approximate weight amounts of 0.05 to 4%, preferably 0.05 to 3%, more preferably 0.1 to 2%.

The AEA may also comprise natural anionic polymeric polycarboxylates containing retention-enhancing groups carboxymethyl cellulose and other binding agents gums and film-formers devoid of the above-defined delivery-enhancing and/or retention-enhancing groups are ineffective as AEA's.

As illustrative of AEA's containing phosphinic acid and/or sulfonic acid delivery enhancing groups, there may be mentioned polymers and copolymers containing units or moieties derived from the polymerization of vinyl or allyl phosphinic and/or sulfonic acids substituted as needed on the 1 or 2 (or 3) carbon atom by an organic retention-enhancing group, for example having the formula —$(X)_n$—R defined above. Mixtures of these monomers may be employed, and copolymers thereof with one or more inert polymerizable ethylenically unsaturated monomers such as those described above with respect to the operative synthetic anionic polymeric polycarboxylates. As will be noted, in these and other polymeric AEA's operative herein, usually only one acidic delivery-enhancing group is bonded to any given carbon or other atom in the polymer backbone or branch thereon. Polysiloxanes containing pendant delivery-enhancing groups and retention enhancing groups may also be employed as AEA's herein. Also effective as AEA's herein are ionomers containing or modified to contain delivery- and retention-enhancing groups. Ionomers are described on pages 546–573 of the Kirk-Othmer Encyclopedia of Chemical Technology, third edition, Supplement Volume, John Wiley & Sons, Inc. copyright 1984, which description is incorporated herein by reference. Also effective as AEA's herein, provided they contain rare modified to certain retention-enhancing groups, are polyesters, polyurethanes and synthetic and natural polyamides including proteins and proteinaceous materials such as collagen, poly (argenine) and other polymerized amino acids.

Without being bound to a theory, it is believed that the AEA, especially polymeric AEA, is generally an anionic film forming material and is thought to attach to tooth surfaces and form a continuous film over the surfaces, thereby preventing bacterial attachment to tooth surfaces. It is possible that the noncationic antibacterial agent forms a complex or other form of association with the AEA, thus forming a film of a complex or the like over tooth surfaces. The film forming property of the AEA and the enhanced delivery and film forming property of the AEA and the enhanced delivery and retention of the antibacterial agent on tooth surfaces due to the AEA appears to make tooth surfaces unfavourable for bacterial accumulation particularly since the direct bacteriostatic action of the antibacterial agent controls bacterial growth. Therefore, through the combination of three modes of actions: 1) enhanced delivery, 2) long retention time on tooth surfaces, and 3)

prevention of bacterial attachment to tooth surfaces, the oral composition is made efficacious for reducing plaque. Similar antiplaque effectiveness is attained on soft oral tissue at or near the gum line.

In aforementioned application Ser. No. 398,606, filed on date herewith, titled "Antibacterial Antiplaque Oral Compositions" wherein the dentifrices thereof contain about 5-30% by weight of a siliceous polishing agent, a material which solubilizes the noncationic antibacterial agent to render it effective in delivery to soft oral tissues at the gum line is employed. In the present invention, when the amount of the noncationic antibacterial agent is optimized at about 0.25-0.35% by weight, it is found that the solubilizing agent is not required; but is rather optional.

In the oral preparation dentifrice, an orally acceptable vehicle including a water-phase with humectant is present. Water is present typically an amount of at least about 3% by weight, generally about 3-35% and humectant, preferably glycerine and/or sorbitol, typically total about 6.5-75% or 80% by weight of the oral preparation dentifrice, more typically about 10-75%. Reference hereto to sorbitol refers to the material typically as available commercially in 70% aqueous solutions. Although not required in the present invention wherein about 0-25-0.35% of the water insoluble non-cationic antibacterial agent is present optionally, an additional ingredient which assists solubilization of the antibacterial agent in saliva may be incorporated in the water-humectant vehicle. Such optional solubilizing agents include humectant polyols such as propylene glycol, dipropylene glycol, and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate. As used herein "propylene glycol" includes 1,2-propylene glycol and 1,3-propylene glycol. Significant amounts of polyethylene glycol particularly of molecular weight of 600 or more should be avoided since polyethylene glycol effectively inhibits the antibacterial activity of the noncationic antibacterial agent. For instance, polyethylene glycol (PEG) 600 when present with triclosan in a weight ratio of 25 triclosan:1 PEG 600 reduces the antibacterial activity of triclosan by a factor of about 16 from that prevailing in the absence of the polyethylene glycol.

The pH of such oral preparation dentifrice of the invention is generally in the rental range of about 4.5 to about 9 or 10 and not preferably about 6.5 to about 7.5. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In this invention, the oral composition dentifrice may be substantially gel in character, such as a gel dentifrice. Such gel oral preparations contain siliceous dentally polishing material. Preferred polishing materials include crystalline silica having particle sized of up to about 5 microns, a mean particle size of up to about 1.1 microns, and a surface area of up to about 50,000 cm.$^2$/gm., silica gel or colloidal silica and complex amorphous alkali metal aluminosilicate.

When visually clear or opacified gels are employed, a polishing agent of colloidal silica, such as those sold under the trademark SYLOID as Syloid 72 and Syloid 74 or under the trademark SANTOCEL as Santocel 100 or alkali metal almuinosilicate complexes (that is, silica containing alumina combined in its matrix) are particularly useful, since they are consistant with gel-like texture and have refractive indices close to the refractive indices of gelling agent-liquid (including water and/or humectant)systems commonly used in dentifices.

The polishing material is generally present in the oral composition dentifrices such as toothpaste or gel compositions in weight concentrations of about 5% to about 30%.

In a gel toothpaste, the liquid vehicle may typically comprise about 3-35% by weight of water, such as about 10-35%, and humectant in an amount ranging from about 6.5% to about 80%, such as about 10% to about 80% by weight of the preparation. In clear gels where the refractive index is an important consideration, about 3-30% of water, 0 to about 70% of glycerine and about 20-25% of sorbitol are preferably employed.

The oral composition dentifrices typically contain a natural or synthetic thickener or gelling agent in proportions of about 0.1 to about 10%, preferably about 0.5 to about 5%. A suitable thickener is synthetic hectorite, a synthetic colloidal magnesium alkali metal silicate complex clay available for example as Laponite (e.g. CP, SP 2002,D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable gelling agents or thickeners include Irish moss, i-carrageenan, gum tragacanth, starch, polyvinylpyrrolidone, hydroxyethypropyl-cellulose, hydroxybutyl methyl cellulose, hydroxypropyl methyl cellulose, hydroxyethyl cellulose (e.g. available as Natrosol), sodium carboxymethyl cellulose, and colloidal silica such those available as finely ground Syloid 244 and Sylodent 15.

There may be a tendency for the dentifrice to separate into liquid and solid portions when about 5% by weight or more of the optional solubilizing material such as propylene glycol is present. Furthermore, in the present invention excellent antiplaque effects can be obtained with small amounts of antibacterial agent which do not even require solubilizing agent. In the present invention, a preferred dentifrice contains about 0.3% by weight of the antibacterial agent and about 1.5-2% by weight of the polycarboxylate.

Without being bound to a theory whereby the advantages of this invention are achieved, it is believed that an aqueous, humectant vehicle is normally solubilized in surfactant micelles in the mobile phase (that is, not including gelling agent and polishing agent) of a dentfrice formula. The mobile phase solution of dentifrice during use can become diluted with saliva which causes triclosan to precipitate. However, in the present invention, it is found that even in the absence of a special solubilizing material for triclosan, when the amount of triclosan is about 0.25%-0.35% by weight and the polycarboxylate is present, sufficient triclosan is present to exert an excellent antiplaque effect on the soft tissues at the gum line. Similar remarks apply to other water-insoluble noncationic antibacterial agents herein described.

The oral composition dentifrice may also contain a source of fluoride ions, or fluorine-providing component, as anti-caries agent, in an amount sufficient to supply about 25 ppm to 5,000 ppm of fluoride ions. These compounds may be slightly soluble in water or may be fully water-soluble. They are characterized by their ability to release fluoride ions in water and by substantial freedom from undesired reaction with other compounds of the oral preparation. Among these materials are inorganic fluoride salts, such as soluble alkali metal, alkaline earth metal salts, or example, sodium fluoride, potassium fluoride, ammonium fluoride, calcium fluoride, a copper fluoride such as cuprous fluoride, zinc fluoride, barium fluoride, sodium flourosilicate, ammonium flourosilicate, sodium fluorozirconate, ammonium fluorozirconate, sodium monofluorophosphate, aluminum mono-and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral preparation, but it must be a non-toxic amount, generally about 0.0005 to about 3.0% in the preparation. In a dentifrice preparation, e.g. dental gel and an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferably about 800 to about 1,500 ppm of fluoride ion.

Typically, in the cases of alkali metal fluorides, this component is present in an amount up to about 2% by weight, based on the weight of the preparation, and preferably in the range of about 0.05% to 1%. In the case of sodium monofluorophosphate, the compound may be present in an amount of about 0.1-3%, more typically about 0.76%.

It will be understood that, as is conventional, the oral preparations are to be sold or otherwise distributed in suitable labelled packages. Thus a dentifrice gel will usually be in a collapsible tube, typically aluminum, lined lead or plastic, or other squeeze, pump or pressurized dispenser for metering out the contents, having a label describing it, in substance, as a dentifrice gel or the like.

Organic surface-active agents are used in the compositions of the present invention to achieve increased prophylactic action. Moreover, they assist in achieving thorough and complete dispersion of the antiplaque antibacterial agent throughout the oral cavity, and render the instant compositions more cosmetically acceptable. Indeed, at least one of surface-active agent or flavoring oil is present to effect desired the solubilization of the antibacterial agent. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monosterate) and polypropyleneoxide (e.g. Pluronic materials).

Surface active agent is typically present in amount of about 0.5-5% by weight, prefereably about 1-2.5%. As indicated, surface-active agent is believed to assist in dissolving the noncationic antibacterial agent.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, which are generally soluble and which would complex with active components of the instant invention are to be avoided.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, xylitol, sodium cyclamate, perillartine, AMP (aspartyl phenyl alanine, methyl ester), saccharine and the like. Suitably, flavor and sweetening agents may each or together comprise from about 0.1% to 5% more of the preparation. Moreover, flavoring oil is believed to aid the dissolving of the antibacterial agent, together with or even in the absence of surface-active agent.

In the preferred practice of this invention an oral composition dentifrice containing the composition of the present invention is preferably applied regularly to dental enamel and soft oral tissues, particularly at or near the gum line, such as every day or every second or third day or preferably from 1 to 3 times daily, at a pH of about 4.5 to about 9, generally about 5.5 to about 8, preferably about 6 to 8, for at least 2 weeks up to 8 weeks or more up to lifetime.

The compositions of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticizers or softeners, sugar or other sweeteners or carbohydrates such as glucose, sorbitol and the like.

The following examples are further illustrative of the nature of the present invention, but it is understood that the invention is not limited thereto. All amounts and proportions referred to herein and in the appended claims are by weight, unless otherwise indicated.

EXAMPLE 1

The following dentifrice is prepared:

|  | Parts A | Parts B |
|---|---|---|
| Glycerine | 10.00 | — |
| Propylene Glycol | — | 10.00 |
| Sorbitol (70%) | 25.00 | 25.00 |
| Iota carrageenan | 0.60 | 0.60 |
| Gantrez S-97 | 2.00 | 2.00 |
| Sodium Saccharin | 0.40 | 0.40 |
| Sodium Fluoride | 0.243 | 0.243 |
| Sodium Hydroxide (50%) | 1.00 | 1.00 |
| Titanium Oxide | 0.50 | 0.50 |
| Silica Polishing Agent (Zeodent 113) | 20.00 | 20.00 |
| Silica Thickener (Sylox 15) | 5.50 | 5.50 |
| Sodium Lauryl Sulfate | 2.00 | 2.00 |
| Water | 31.507 | 31.507 |
| Tricolosan | 0.30 | 0.30 |
| Flavor Oil | 0.95 | 0.95 |

The above dentifrice A delivers Triclosan to the teeth and soft gum tissue essentially as well as dentifrices B containing a special solubilizing agent for Triclosan. In other words, a special solubilizing agent is not required for the dentifrice of the present invention to be effective. Further, a corresponding dentifrice in which the Gantrez polycarboxylate is absent is substantially poorer in delivering Triclosan.

In the foregoing example, improved results may also be obtained by replacing triclosan with other antibacterial agents herein described such as phenol, thymol, eugenol and 2.2'-methylene bis (4-chloro-6-bromophenol) and/or by replacing Gantrez with other AEA's such as a 1:1 copolymer of maleic anhyride and ethyl acrylate, sulfoacrylic oligomers, Carbopols (e.g. 934), and polymers of alpha or beta-styrenephosphonic acid monomers and copolymers of these monomers with each or with other ethylenically unsaturated polymerizable monomers such as vinyl phosphonic acid.

EXAMPLE 2

The following liquid phase dentifrice solutions are tested for uptake and retention of triclosan on saliva coated HA disks following the test procedures described in Example 1 with the indicated results:

| Ingredients | A | B | C | D |
|---|---|---|---|---|
| Sorbitol (70% solution) | 30.0 | 30.0 | 30.0 | 30.0 |
| Glycerol | 9.5 | 9.5 | 9.5 | 9.5 |
| Propylene Glycol | 0.5 | 0.5 | 0.5 | 0.5 |
| SLS | 20.0 | 20.0 | 20.0 | 20.0 |
| NaF | 0.243 | 0.243 | 0.243 | 0.243 |
| Flavor Oil | 0.95 | 0.95 | 0.95 | 0.95 |
| Triclosan | 0.3 | 0.3 | 0.3 | 0.3 |
| Water | 56.507 | 54.507 | 54.507 | 54.507 |
| Poly (beta-styrenephosphonic acid) |  | 2.0 |  |  |
| Poly (alpha-styrenephosphonic acid) |  |  | 2.0 |  |
| Polyvinyl Alcohol |  |  |  | 2.0 |
| Adjusted to pH 6.5 with NaOH Triclosan Uptake in Micrograms on Saliva Coated Disks | 31.0 | 174.0 | 86.0 | 36.0 |
| Retention of Triclosan on Saliva Coated HA Disks After: |  |  |  |  |
| Initial |  | 183.0 |  |  |
| 30 minutes |  | 136.0 |  |  |
| 1 hour |  | 105.0 |  |  |
| 3 hours |  | 83.0 |  |  |

The above results show that solution (D) containing polyvinyl alcohol, not an AEA hereunder, produced a triclosan uptake of only 36.0, quite similar to the 31.0 uptake of the control solution (A) without additive. In contrast, solution (C) with poly (alpha-styrenephosphonic acid) produces an uptake of 86.0, more than double that of solutions (A) and (D), and solution (B) with poly (beta-styrenephosphonic acid) produces an uptake about 5 times that of solutions (A) and (D), tending to indicate further that vicinal substitution of the delivery-enhancing group yields superior results. The above results also show the surprisingly good retention of triclosan on the HA disks over time obtained with solution (B) containing poly (beta-styrenephosphonic acid (M.W's about 3,000 to 10,000).

This invention has been described with respect to certain preferred embodiments and it will be understood that modifications and variations thereof obvious to those skilled in the art are to be included within the purview of this application and the scope of the appended claims.

We claim:

1. An oral composition for attaching, adhering or bonding a plaque-inhibiting agent to oral tooth and gum surface comprising in an orally acceptable aqueous humectant vehicle, about 5–30% by weight of a siliceous polishing agent, about 0.25%–0.35% by weight of a substantially water insoluble noncationic antibacterial agent, said oral composition comprising at least one of a surface active agent and a flavoring oil and about 0.05–4% by weight of an antibacterial-enhancing agent which contains at least one delivery-enhancing functional group and at least one organic retention-enhancing group, wherein said delivery-enhancing group enhances delivery of said antibacterial agent to oral tooth and gum surfaces and said retention-enhancing group enhances attachment, adherence or bonding of said antibacterial agent on oral tooth and gum surfaces, wherein said oral composition is free of polyphosphate anticalculus agent in an effective anticalculus amount and said vehicle is other than polyethylene glycol which reduces the antibacterial activity of said antibacterial agent.

2. The oral composition claimed in claim 1 wherein said antibacterial agent is selected from the group consisting of halogenated diphenyl ethers, halogenated salicylanilides, benzoic esters, halogenated carbanilides and phenolic compounds.

3. The oral composition claimed in claim 2 wherein said antibacterial agent is a halogenated diphenyl ether.

4. The oral composition claimed in claim 3 wherein said halogenated diphenyl ether is 2,4,4'-trichloro-2'-hydroxyphenyl ether.

5. The oral composition claims in any one of claims 1 to 4 wherein said surface active agent is present in amount of about 0.5-5% by weight.

6. The oral composition claims in any one of claims 1 to 4 wherein said flavoring oil is present in amount of about 0.1-5% by weight.

7. The oral composition according to any one of claims 1 to 4 wherein said antibacterial-enhancing agent has an average molecular weight of about 100 to about 1,000,000.

8. The oral composition according to claim 7 wherein said delivery-enhancing group is acidic.

9. The oral composition according to claim 8 wherein said delivery-enhancing group is selected from the group consisting of carboxylic, phosphoric, phosphinic, and sulfonic acids, and salts, and mixtures thereof and wherein said organic retention-enhancing group comprises the formula $-(X)_n-R$ wherein X is O, N, S, SO, $SO_2$, P, PO or Si, R is hydrophobic alkyl, aryl, alkaryl, alkenyl, acyl, aralkyl, heterocyclic, or inert-substituted derivatives thereof, and n is zero or 1 or more and wherein said antibacterial-enhancing agent is a natural or synthetic monomer or a polymer selected from the group consisting of oligomers, homopolymers, copolymers of two or more monomers, ionomers, block copolymers, graft copolymers and cross-linked polymers and monomers.

10. The oral composition according to claim 9 wherein said antibacterial-enhancing agent is an anionic polymer containing a plurality of said delivery-enhancing and retention-enhancing groups.

11. The oral composition according to claim 10 wherein said anionic polymer comprises a chain containing repeating units each containing at least one carbon atom.

12. The oral composition according to claim 11 wherein the unit contains at least one delivery-enhancing group and at least one retention-enhancing group bonded to the same, vicinal, or other atoms in the chain.

13. The oral preparation according to claim 9 wherein the delivery-enhancing group is a phosphonic group or salt thereof.

14. The oral composition according to claim 13 wherein said antibacterial-enhancing agent is poly (beta-styrenephosphonic acid), poly (alpha-styrenephosphonic acid) polymer, or copolymer of either styrenephosphonic acid with the other or with another ethylenically unsaturated polymerizable monomer.

15. The oral composition according to any one of claims 1 to 4 containing a fluoride-providing source.

* * * * *